United States Patent [19]

Rasberger et al.

[11] 4,317,911

[45] Mar. 2, 1982

[54] PIPERIDINE CONTAINING CYANURIC ACID DERIVATIVES

[75] Inventors: Michael Rasberger, Riehen; Friedrich Karrer, Zofingen, both of Switzerland

[73] Assignee: Ciba-Geigy Corporation, Ardsley, N.Y.

[21] Appl. No.: 812,295

[22] Filed: Jul. 1, 1977

[30] Foreign Application Priority Data

Jul. 8, 1976 [CH] Switzerland .......................... 8776/76

[51] Int. Cl.³ .......................................... C07D 401/74
[52] U.S. Cl. ................................... 544/222; 544/221; 524/101
[58] Field of Search .......................................... 544/222

[56] References Cited

U.S. PATENT DOCUMENTS 4,118,369  10/1978  Minagawa et al. ............ 260/45.8 N

FOREIGN PATENT DOCUMENTS 51-88484  8/1976  Japan ................................... 544/222

*Primary Examiner*—Richard A. Schwartz
*Attorney, Agent, or Firm*—Wenderoth, Lind & Ponack

[57] ABSTRACT

New cyanuric acid derivatives containing at least one hindered phenolic moiety and at least one hindered amine moiety are effectful light stabilizers and antioxidants for polymeric materials.

14 Claims, No Drawings

PIPERIDINE CONTAINING CYANURIC ACID DERIVATIVES

The present invention relates to new piperidine derivatives of cyanuric acid, their manufacture, their use as stabilisers for organic material and to the organic material stabilised with the aid thereof.

The use of tris-hydroxyaralkyl isocyanurates as light stabilisers for organic polymers is known from British Pat. Specification No. 1,348,093. Furthermore, it is known to employ sterically hindered amines as light stabilisers in organic materials; thus, tris-piperidinyl-1,3,5-triazine stabilisers are described, for example in British Pat. Specification No. 1,393,551.

A new class of piperidinyl isocyanurates, which is distinguished by a good light stabilising activity, has now been found.

The invention thus relates to the new compounds of the general formula

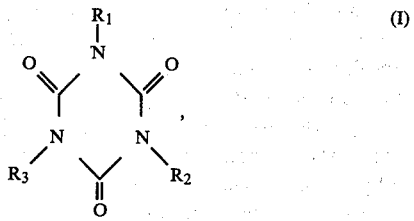

and to addition salts thereof,
in which $R_1$ denotes

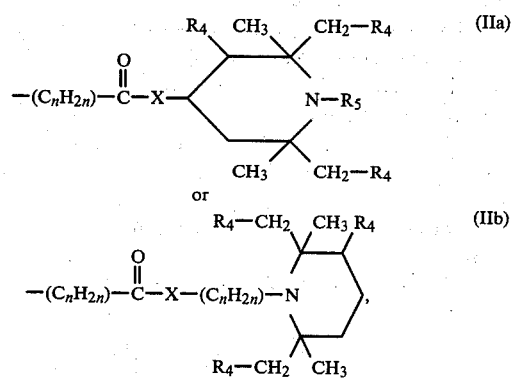

and $R_2$ and $R_3$ independently of one another denote hydrogen, a group of the formula (IIa or b) or addition salts thereof, or $-CH_2R_{11}$, wherein n is 1, 2, 3, 4 or 5, $R_4$ is hydrogen or $C_1-C_8$ alkyl and $R_5$ is hydrogen, oxyl, $C_1-C_{12}$ alkyl, $C_3-C_6$ alkenyl, $C_3-C_4$ alkinyl, $C_2-C_{21}$ alkoxyalkyl, $C_7-C_9$ aralkyl, 2,3-epoxypropyl, an aliphatic acyl group with 1-4 C atoms or one of the groups $-CH_2COOR_6$, $-CH_2-CH(R_7)-OR_8$, $-COOR_9$ or $-CONHR_9$, wherein $R_6$ is $C_1-C_{12}$ alkyl, $C_3-C_6$ alkenyl, phenyl, $C_7-C_8$ aralkyl or cyclohexyl, $R_7$ is hydrogen, methyl or phenyl, $R_8$ denotes hydrogen, an aliphatic, aromatic, araliphatic or alicyclic acyl group with 1-18 C atoms, wherein the aromatic part, if appropriate, can be substituted by chlorine, $C_1-C_4$ alkyl, $C_1-C_8$ alkoxy and/or by hydroxyl, and $R_9$ denotes $C_1-C_{12}$ alkyl, cyclohexyl, phenyl or benzyl and X is $-O-$ or $-NR_{10}-$ wherein $R_{10}$ is hydrogen or $C_1-C_{12}$ alkyl, and $R_{11}$ is one of the groups

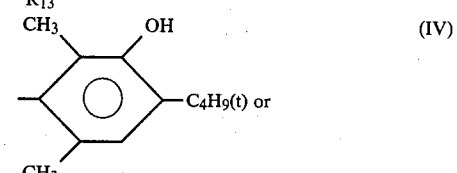

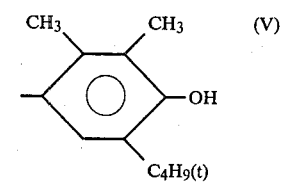

wherein $R_{12}$ and $R_{13}$ independently of one another denote $C_1-C_{12}$ alkyl, $C_5-C_{12}$ cycloalkyl, $C_7-C_9$ aralkyl or $C_7-C_{12}$ alkaryl.

If $R_1$, $R_2$ and $R_3$ in the formula I denote a group of the formula II, examples of $R_4$ as $C_1-C_8$ alkyl are methyl, ethyl, isopropyl, n-butyl, amyl, n-hexyl or n-octyl. Alkyl groups with 1-4 C atoms, and especially ethyl and methyl or hydrogen are preferred. Compounds in which $R_4$ denotes hydrogen are to be singled out in particular.

Examples of $R_5$ as $C_1-C_{12}$ alkyl are methyl, ethyl, n-propyl, n-butyl, n-pentyl, n-hexyl, n-octyl, n-decyl or n-dodecyl. Alkyl groups with 1-8 C atoms, in particular those with 1-4 C atoms and above all methyl, are preferred.

Examples of $R_5$ as $C_3-C_6$ alkenyl are allyl, 2-butenyl or 2-hexenyl, especially allyl.

An example of $R_5$ as $C_3-C_4$ alkinyl is propargyl.

If $R_5$ denotes $C_2-C_{21}$ alkoxyalkyl, the alkyl part can contain 1-3 C atoms and the alkoxy part can consist of 1-18 C atoms, such as, for example, in methoxymethyl, ethoxymethyl, 2-methoxyethyl, 2-ethoxyethyl, 2-n-butoxyethyl, 3-n-butoxyethyl, 2-octoxyethyl or 2-octadecyloxyethyl, and compounds in which $R_5$ denotes an alkoxy group with 2-6 C atoms should be especially mentioned.

Examples of $R_5$ as $C_7-C_9$ aralkyl are benzyl or α-phenylethyl.

Examples or $R_5$ as an aliphatic acyl group with 1-4 C atoms are formyl, acetyl, acryloyl or crotonyl, especially acetyl.

If $R_5$ is the group $-CH_2COOR_6$, $R_6$ as $C_1-C_{12}$ alkyl denotes, for example, methyl, ethyl, isopropyl, n-butyl, isobutyl, t-butyl, isopentyl, n-octyl, n-decyl or n-dodecyl. Preferably $R_6$ is $C_1-C_4$ alkyl, and examples of $R_6$ as $C_3-C_6$ alkenyl are allyl, 2-butenyl or 2-hexenyl. Examples of $R_6$ as $C_7-C_8$ aralkyl are benzyl or α-phenylethyl.

If $R_5$ is the group $-CH_2-CH(R_7)-OR_8$, $R_7$ denotes hydrogen, methyl or phenyl, especially hydrogen. Examples of $R_8$ as an aliphatic, aromatic, alicyclic or araliphatic $C_1-C_{18}$ acyl radical which is substituted in the aromatic part, if appropriate, by chlorine, $C_1-C_4$ alkyl, such as methyl, ethyl, n-propyl or t-butyl, or by $C_1-C_8$ alkoxy, such as methoxy, ethoxy, butoxy or octoxy, and/or by hydroxyl, are acetyl, propionyl, butyryl, octanoyl, dodecanoyl, stearoyl, acryloyl, benzoyl, chlorobenzoyl, toluoyl, isopropylbenzoyl, 2,4-dichlorobenzoyl, 4-methoxybenzoyl, 3-butoxybenzoyl, 2-hydroxybenzoyl, 3,5-di-t-butyl-4-hydroxybenzoyl, β-(3,5-di-t-butyl-4-hydroxyphenyl)-propionyl, phenylacetyl, cinnamoyl or hexahydrobenzoyl.

If $R_5$ is the group —$COOR_9$, examples of $R_9$ as $C_1$–$C_{12}$ alkyl are methyl, ethyl, isobutyl, n-hexyl, n-octyl, n-decyl or n-dodecyl. Alkyl groups with 1–4 C atoms are preferred as $R_9$.

If $R_5$ is —$CONHR_9$, $R_9$ is especially cyclohexyl or phenyl.

X is —O— or —$NR_{10}$—, preferably —O—, and examples of $R_{10}$ as $C_1$–$C_{12}$ alkyl are methyl, ethyl, n-butyl, n-hexyl, n-octyl, n-decyl or n-dodecyl.

If $R_{11}$ denotes a group of the formula III, examples of $R_{12}$ and $R_{13}$ as $C_1$–$C_{12}$ alkyl are methyl, ethyl, t-butyl, n-hexyl, n-octyl, n-decyl or n-dodecyl. Alkyl groups with 1–4 C atoms and especially t-butyl should be singled out above all.

The values of n relate to $C_nH_{2n}$ groups, but for various $C_nH_{2n}$ groups they are independent of one another (formula IIb).

Salts which may be mentioned of the compounds are especially acid addition salts with inorganic or organic acids. The salts can be obtained in the customary manner and the free bases which in turn are preferred can be recovered from the salts. Acids which are suitable for forming salts are in particular inorganic acids, such as hydrochloric acid, sulphuric acid and phosphoric acid but also organic acids, such as, for example, p-toluene-sulphonic acid.

Those compounds of the formula I are preferred, in which $R_1$ is a group of the formula IIa, $R_2$ and $R_3$ independently of one another denote a group of the formula IIa or —$CH_2$—$R_{11}$, n is 1, 2, 3, 4 or 5, $R_4$ is hydrogen or $C_1$–$C_4$ alkyl and $R_5$ is hydrogen, oxyl, $C_1$–$C_8$ alkyl, $C_3$–$C_4$ alkenyl or alkinyl, $C_2$–$C_6$ alkoxyalkyl, $C_7$–$C_9$ aralkyl, acetyl, acryloxy or crotonoyl or one of the groups —$CH_2$—$COOR_6$, —$CH_2$—$CH(R_7)$—$OR_8$, —$COOR_9$ or —$CONHR_9$, wherein $R_6$ is $C_1$–$C_4$ alkyl, $C_3$–$C_4$ alkenyl, phenyl, $C_7$–$C_8$ aralkyl or cyclohexyl, $R_7$ is hydrogen, methyl or phenyl, $R_8$ denotes hydrogen or an aliphatic, aromatic, alicyclic or araliphatic acyl group with 1–18 C atoms, wherein the aromatic part, if appropriate, can be substituted by chlorine, $C_1$–$C_4$ alkyl, $C_1$–$C_8$ alkoxy and/or hydroxyl, $R_9$ is $C_1$–$C_{12}$ alkyl, X is —O— or —$NR_{10}$— wherein $R_{10}$ denotes hydrogen or $C_1$–$C_{12}$ alkyl, and $R_{11}$ is one of the groups of the formula III, IV or V, wherein $R_{12}$ and $R_{13}$ independently of one another denote $C_1$–$C_8$ alkyl, $C_5$–$C_6$ cycloalkyl or $C_7$–$C_9$ aralkyl.

Those compounds of the formula I are particularly preferred, in which $R_1$ is a group of the formula IIa, $R_2$ and $R_3$ independently of one another are a group of the formula IIa or —$CH_2$—$R_{11}$, n is 1, 2 or 3, $R_4$ denotes hydrogen or methyl, $R_5$ is hydrogen, $C_1$–$C_4$ alkyl, allyl, propargyl, $C_2$–$C_6$ alkoxyalkyl, acetyl, acryloyl or crotonoyl or one of the groups —$CH_2$—$COOR_6$, —$CH_2$—$CH(R_7)$—$OR_8$, —$COOR_9$ or —$CONHR_9$ wherein $R_6$ is $C_1$–$C_4$ alkyl, $R_7$ denotes hydrogen or methyl, $R_8$ denotes hydrogen and $R_9$ is $C_1$–$C_4$ alkyl, X is —O— or —$NR_{10}$— wherein $R_{10}$ is hydrogen or methyl, and $R_{11}$ is a group of the formula III, IV or V wherein $R_{12}$ and $R_{13}$ independently of one another denote $C_1$–$C_4$ alkyl.

Compounds which are of quite special interest and which have a good action are those of the formula I, according to Claim 1, wherein n is 1 and $R_1$ corresponds to the formula IIa.

In second place are preferred also the above particularly preferred definitions, with $R_1$, $R_2$ and/or $R_3$ corresponding however to the formula IIb.

Examples of compounds of the general formula I are: 1,3,5-tris-[2-(2,3,6-trimethyl-2,6-diethyl-piperidin-4-yl-oxycarbonyl)ethyl]-isocyanuric acid, 1,3,5-tris-[4-(2,2,6,6-tetramethyl-piperidin-4-yl-iminocarbonyl)-n-butyl]-isocyanuric acid, 1,3,5-tris-[3-(2,3,6-trimethyl-2,6-diethyl-N-acetylpiperidin-4-yl-oxycarbonyl)-propyl]-isocyanuric acid, 1,3-di-[2-(1,2,2,6,6-pentamethyl-piperidin-4-yl-oxycarbonyl)-ethyl]-5-[3,5-di-t.butyl-4-hydroxybenzyl]-isocyanuric acid, 1,3,5-tris-[2-(2,2,6,6-tetramethyl-N-acetyl-piperidin-4-yl-iminocarbonyl)-ethyl]-isocyanuric acid, 1,3-di-[4-(2,2,6,6-tetramethyl-piperidin-4-yl-oxycarbonyl)-n-butyl]-5-[2,6-dimethyl-4-t.butyl-3-hydroxybenzyl]-isocyanuric acid, 1,3-di-[2-(2,3,6-trimethyl-2,6-diethyl-N-acetylpiperidin-4-yl-oxycarbonyl)-ethyl]-5-[2,3-dimethyl-5-t.butyl-4-hydroxybenzyl]-isocyanuric acid, 1,3,5-tris-[(1,2,2,6,6-pentamethyl-piperidin-4-yl-oxycarbonyl)-methyl]-isocyanuric acid, 1,3,5-tris-[3-(2,2,6,6-tetramethyl-N-acryloylpiperidin-4-yl-iminocarbonyl)-n-propyl]-isocyanuric acid, 1,3-di-[2-(2,2,6,6-tetramethyl-N-acetyl-piperidin-4-yl-oxycarbonyl)-ethyl]-5-[2-(2,3,6-trimethyl-2,6-diethyl-piperidin-4-yl-iminocarbonyl)-ethyl]-isocyanuric acid, 1,3-di-[5-(2,2,6,6-tetramethyl-piperidin-4-yl-oxycarbonyl)-n-pentyl]-5-[3-methyl-5-t.butyl-4-hydroxybenzyl]-isocyanuric acid, 1,3-di-[3,5-di-t.butyl-4-hydroxybenzyl]-5-[(2,2,6,6-tetramethyl-piperidin-4-yl-oxycarbonyl)-methyl]-isocyanuric acid, 1,3,5-tris-[(2,3,6-trimethyl-2,6-diethyl-N-acetyl-piperidin-4-yl-iminocarbonyl)-methyl]-isocyanuric acid and 1,3-di-[2-(2,2,6,6-tetramethyl-piperidin-4-yl-oxycarbonyl)-ethyl]-5-[2,6-dimethyl-4-t.butyl-3-hydroxybenzyl]-isocyanuric acid.

The compounds of the formula I can be manufactured by various processes which are in themselves known.

Most simply, they are manufactured by classical esterification or amidisation reactions wherein a compound of the formula VI

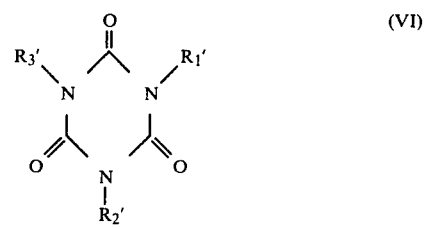

in which at least one of the radicals $R_1'$, $R_2'$ and $R_3'$ denotes a group of the formula VII

wherein Y denotes one of the groups —$COOR_{14}$, —COHal or —CN, wherein $R_{14}$ denotes hydrogen or preferably $C_1$–$C_4$ alkyl, Hal is chloride, bromide or iodide and the remaining radicals $R_1'$, $R_2'$ and $R_3'$ have the meaning of $R_1$, $R_2$ and $R_3$, is reacted with a compound of the formula VIIIa or b

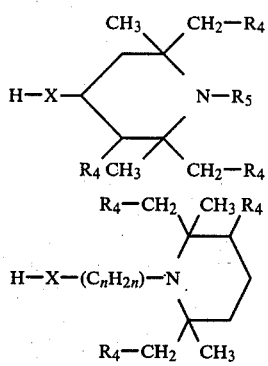 (VIIIa)

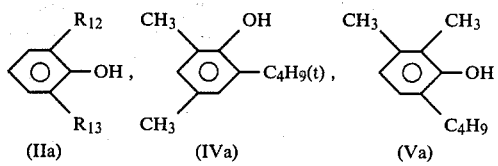

(IIa)   (IVa)   (Va)

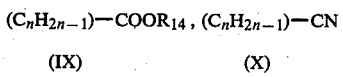 (IIIb)

Depending on the selected molar ratios, monosubstitution or disubstitution results so that two reactive positions or one reactive position respectively are left free for the introduction of a group of the formula VII.

In a variant of the process, a radical —CH$_2$—R$_{11}$ is introduced by reacting approximately one or two mols of a halogen-containing phenol of the formulae The addition reaction of a group VII with isocyanuric acid is, for example, carried out by reacting isocyanuric acid with an unsaturated ester of the formula IX or a corresponding nitrile of the formula X $(C_nH_{2n-1})$—COOR$_{14}$, $(C_nH_{2n-1})$—CN (IX)   (X)

in the presence of a base and preferably in a solvent. Preferably, the unsaturated radical contains a terminal double bond.

Depending on the selected molar ratio of isocyanuric acid to ester or nitrile of the formula IX and X, monosubstitution, disubstitution or trisubstitution can be achieved in the manner described. Thus, compounds of the formula XI

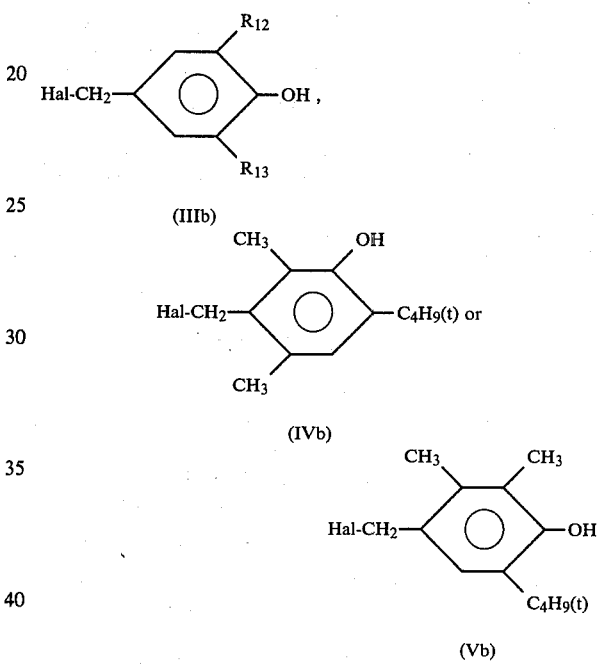

(IIIb)

(IVb)

(Vb)

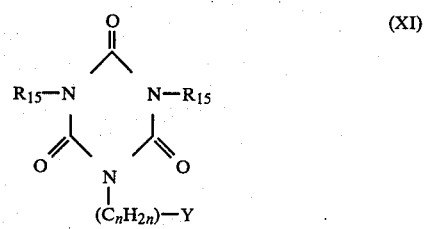 (XI)

in which R$_{15}$ denotes hydrogen or the group —(C$_n$H$_{2n}$)—COOR$_{14}$, are obtained.

In a variant of the process, isocyanuric acid can also be reacted with a halide of the formula XII

Hal—(C$_n$H$_{2n}$)—COOR$_{14}$   (XII)

in the presence of a base, such as an alkali metal hydroxide or alkali metal oxide. Bromide, chloride and iodide are suitable for use as the halide. Esters of the formula XI are formed in this process.

A group of the formula II is usually introduced by reacting a compound of the formula XI with the desired amount of a compound of the formula VIIIa or b.

A group of the formula —CH$_2$—R$_{11}$ is likewise introduced by known methods. Thus, the reaction of isocyanuric acid with formaldehyde and a phenol in DMF is described, for example in DT-OS No. 1,853,143. The phenols employed for preparing the present compounds are compounds of the formulae with approximately 3 mols of potassium cyanate KOCN, the isocyanuric acid ring being closed at the same time and, depending on the molar ratio, monosubstitution or disubstitution occurring.

In a further variant of the process, cyanuric acid is reacted with sodium hydroxide in DMF, the mono-, di- or tri-sodium salt being obtained. This salt can conveniently be reacted with a halide of the formula XII and subsequently with a piperidine of the formula VIIIa/b. If desired, one or two radicals of the formulae III, IV or V can also be introduced in this variant in the manner described above.

In this way, compounds of the formula I, containing radicals of the formula II which are symmetrical or unsymmetrical, can be prepared at will; it is, however, also possible to prepare compounds with mixed substitution, that is to say compounds which contain groups of the formula II and groups of the formula —CH$_2$—R$_{11}$ or hydrogen. In the case of compounds with mixed substitution, it is simpler first to introduce the radicals of the formula —CH$_2$R$_{11}$ and subsequently the radicals of the formula II.

The starting materials of the formulae IX, X, XII, IIIa, IVa, Va or IIIb, IVb and Vb are known compounds and can be prepared, if they are not available for sale, by methods which have long been known.

The piperidines of the formula VIIIa are known, for example 4-hydroxy-piperidines are known from DT-OS No. 2,352,658 and 4-amino-piperidines are known from U.S. Pat. No. 3,684,765. In general, the 4-OH compounds can be manufactured from the corresponding 4-oxopiperidines of the formula XIII

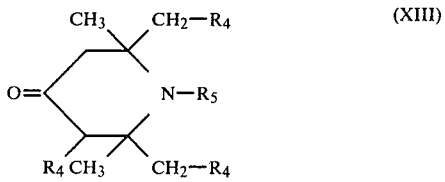 (XIII)

by reduction, for example by catalytic hydrogenation over Raney nickel, whilst the 4—NH₂ compounds are obtainable from compounds of the formula XIII, for example, by means of a reductive conversion with ammonia.

Also the piperidines of the formula VIIIb are known, e.g. from DT-OS No. 2,418,540 and DT-OS No. 2,621,841.

The 4-oxopiperidines of the formula XIII in which R₅ is hydrogen, can be manufactured by various processes.

Thus, for example, W. Traube in Chem. Ber. 41, 777 (1908) describes the reaction of an aliphatic ketone with ammonia.

4-Oxopiperidines of the formula XIII in which R₅ denotes hydrogen, can also be manufactured analogously to the process described in U.S. Pat. No. 3,513,170. Here, an alkyl-substituted tetrahydropyrimidine is hydrolytically rearranged in the presence of an acid catalyst.

N-H compounds of the formula XIII which carry different substituents in the 2-position and 6-position, can be manufactured by reacting a ketone of the formula CH₃—CO—CH₂—R₄ with ammonia. The pyrimidine formed is hydrolysed, as described in Helv. Chim. Acta 30, 114 (1947), to give an aminoketone of the formula XIV.

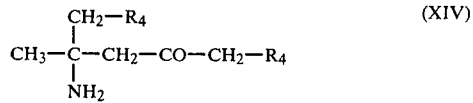 (XIV)

Compounds of the formula XIV are reacted, in a second process stage, with ammonia and a ketone CH₃—CO—CH₂—R₄, as is described, for example, in Monatsh. Chemie 88, 464 (1957). The compounds of the formula VIII in which R₅ denotes hydrogen, can be obtained from the resulting pyrimidine by hydrolysis.

Compounds of the formula XIII in which R₅ does not denote hydrogen, can be manufactured from the corresponding N-H compounds by substitution. This step involves the substitution reactions customary for secondary amines, although these reactions proceed more slowly because of the steric hindrance by the methyl group or the group —CH₂—R₄. For example, the N-H compounds can be reacted with alkyl, alkenyl, aralkyl or alkoxyalkyl halides, dialkyl sulphates, epichlorohydrins, esters of chlorocarboxylic acids, such as esters of chloracetic acid, or acid chlorides or acid anhydrides.

The group —CH₂—CH(R₇)—OR₈ can be introduced by reacting the N-H-piperidines with an epoxide of the formula

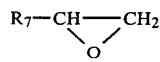

and subsequently acylating the product with an acyl chloride of the formula R₈Cl.

Compounds of the type of 2,2,6,6-tetramethyl-4-(carbalkoxycyanomethyl)-piperidine, which can be used as intermediate products, are moreover known from British Pat. No. 1,214,426.

According to the present invention, the compounds of the formula I can be used as stabilisers for plastics against damage thereto by the action of oxygen, heat and light.

The good light stabilising properties of the new compounds should be particularly singled out. All the compounds of the formula I which contain a radical of the formula III, IV or V, also display, furthermore, a good anti-oxidative activity. The coupled protective effects are industrially useful and have the advantage that the frequently adverse side effects which occur on physical mixing of different stabilisers, disappear.

Examples of plastics which can be stabilised with the new compounds are, for example:

1. Polymers derived from singly or double unsaturated hydrocarbons, e.g. polyolefins such as polyethylene, which if desired may be cross-linked, polypropylene, polybutene-1, polyisobutene, polymethylbutene-1, polymethylpentene-1, polyisoprene, polybutadiene, polystyrene, copolymers of monomers on which the abovementioned homopolymers are based, such as ethylene-propylene copolymers, propylene-butene-1 copolymers, propylene-isobutene copolymers, styrene-butadiene copolymers, and terpolymers of ethylene and propylene with a diene, such as, e.g., hexadiene, dicyclopentadiene, or ethylidenenorbornene; also mixtures of the abovementioned homopolymers, such as, e.g., mixtures of polypropylene and polyethylene, polypropylene and polybutene-1, polypropylene and polyisobutylene; or butadiene-acrylonitrile copolymer mixed with a styrene-butadiene copolymer.
2. Halogen-containing vinyl polymers, such as polyvinyl chloride, polyvinylidene chloride, polyvinyl fluoride, polychloroprene, and chlorinated rubber.
3. Polymers derived from α,β-unsaturated acids and their derivatives, such as polyacrylate and polymethacrylate, polyacrylamide and polyacrylonitrile, and copolymers of the preceding with other vinyl compounds, such as acrylonitrile-butadiene-styrene, acrylonitrile-styrene, and (acrylonitrile-styrene-acrylic ester)copolymers.
4. Polymers derived from unsaturated alcohols and amines and or their acyl or acetal derivatives—such polymers as polyvinyl alcohol, polyvinyl acetate, polyvinyl stearate, polyvinyl benzoate, polyvinyl maleate, polyvinylbutyral, polyallyl phthalate, polyallyl melamine, and copolymers of the preceding with other vinyl compounds, such as ethylene-vinyl acetate copolymers.
5. Homo- and copolymers derived from epoxides, such as polyethylene oxide or polymers derived from bis(glycidyl) ethers.

6. Polyacetals, such as polyoxymethylene and polyoxyethylene, as well as polyoxymethylenes containing ethylene oxide as co-monomer.
7. Polyphenylene oxides.
8. Polyurethanes and polyureas.
9. Polycarbonates.
10. Polysulfones.
11. Polyamides and copolyamides, derived from diamines and dicarboxylic acids and-or from amino carboxylic acids or the corresponding lactams, such as polyamide 6, polyamide 6,6, polyamide 6,10, polyamide 11, and polyamide 12 (nylon 6, etc. are synonymous).
12. Polyesters derived from dicarboxylic acids and dialcohols and-or from hydroxycarboxylic acids or the corresponding lactones, such as polyethylene glycol terephthalate, polybutylene terephthalate, poly-1,4-dimethylolcyclohexane terephthalate; and the starting materials of the preceding, such as lower alkyl esters of the terephthalic acid.
13. Cross-linked polymers derived from aldehydes on the one hand and phenols, ureas and melamines on the other—such as phenol-formaldehyde resins, urea-formaldehyde resins, and melamine-formaldehyde resins.
14. Alkyd resins such as glycerin-phthalic acid resin, and mixtures of these with melamine-formaldehyde resins.
15. Unsaturated polyester resins derived from copolyesters of saturated and unsaturated dicarboxylic acids with polybasic alcohols, along with vinyl compounds as cross-linking agents; and halogen-containing, fire-resistant modifications of these.
16. Natural polymers such as cellulose, rubber, and proteins, and polymer-homologous chemically modified derivatives of the preceding, such as cellulose acetates, cellulose propionates, and cellulose butyrates, and cellulose ethers such as methylcelluloses.

The stabilisation of polyolefines, styrene polymers and polyurethanes is of particular importance and the compounds of the formula I are outstandingly suitable for this purpose. Examples of these are polyethylene of high and low density, polypropylene, ethylene/propylene copolymers, polystyrene, styrene/butadiene/acrylonitrile copolymers, mixtures of polyolefines or of styrene polymers, polyurethanes, based on polyethers or polyesters, in the form of films, lacquers, filaments, elastomers or foams. The compounds of the formula I are particularly suitable for stabilising ABS.

The stabilisers are added to the plastics in a concentration of 0.01 to 5% by weight, calculated on the material to be stabilised. Preferably 0.03 to 1.5, particularly preferably 0.2 to 0.6, % by weight of the compounds, calculated on the material to be stabilised, are incorporated into the latter.

The incorporation can be carried out after the polymerisation, for example by admixing the compounds and, optionally, further additives to the melt by the methods customary in the art, before or during shaping, or by applying the dissolved or dispersed compounds to the polymer, if appropriate with subsequent evaporation of the solvent.

The new compounds can also be added to the plastics to be stabilised in the form of a master batch which contains these compounds, for example in a concentration of 2.5 to 25% by weight.

In the case of crosslinked polyethylene, the compounds are added before crosslinking.

The invention thus also relates to the plastics which have been stabilised by the addition of 0.01 to 5% by weight of a compound of the formula I and which optionally can also contain further known and customary additives. The plastics stabilised in this way can be used in very diverse forms, for example as films, fibres, tapes, profiles or as binders for lacquers, adhesives or cements.

Examples which may be mentioned of further additives which can be employed together with the stabilisers to be used according to the invention are: antioxidants, such as simple 2,6-dialkylphenols, derivatives of alkylated hydroquinones, hydroxylated thiodiphenyl ethers, alkylidene-bisphenols, O-, N- and S-benzyl compounds, hydroxybenzylated malonates, hydroxybenzyl-aromatic compounds, s-triazine compounds, amides of $\beta$-(3,5-di-tert.-butyl-4-hydroxyphenyl)-propionic acid, esters of $\beta$-(3,5-di-tert.-butyl-4-hydroxyphenyl)-propionic acid, esters of $\beta$-(5-tert.-butyl-4-hydroxy-3-methylphenyl)-propionic acid, esters of 3,5-di-tert.-butyl-4-hydroxyphenylacetic acid, acylaminophenols, benzyl-phosphonates and aminoaryl derivatives, UV absorbers and light stabilisers, such as 2-(2'-hydroxyphenyl)-benztriazoles, 2,4-bis-(2'-hydroxyphenyl)-6-alkyl-s-triazines, 2-hydroxybenzophenones, 1,3-bis-(2'-hydroxybenzoyl)-benzenes, esters of optionally substituted benzoic acids and acrylates, and furthermore nickel compounds, sterically hindered amines, oxalic acid diamides, metal deactivators, phosphites, compounds which destroy peroxides, polyamide stabilisers, basic co-stabilisers, PVC stabilisers, nucleating agents or other additives, such as, for example, plasticisers, lubricants, emulsifiers, fillers, carbon black, asbestos, kaolin, talc, glass fibres, pigments, optical brighteners, flameproofing agents and antistatic agents.

Examples of further additives which can be employed together with the stabilisers to be used according to the invention can be found in DT-OS No. 2,427,853 on pages 18–24.

The manufacture and use of the compounds according to the invention is described in more detail in the examples which follow.

EXAMPLE 1a 0.85 g of tetrabutyl ortho-titanate (monomer) was added, whilst stirring, to a solution, which had been heated to 110°–115° C., of 21.5 g (0.05 mol) of 1,3,5-tris-(2-ethoxycarbonylethyl)-isocyanuric acid and 24.5 g (0.15 mol) of 4-hydroxy-1,2,2,6,6-pentamethylpiperidine in 130 ml of anhydrous xylene. Subsequently, whilst simultaneously passing a slow stream of nitrogen through, the reaction mixture was heated up to 135° in the course of 3 hours, during which the liberated ethanol and also xylene distilled off slowly through the attached descending condenser. The temperature is then raised to 145°–150° and most of the xylene is distilled off. The crude product which already solidified as crystals during cooling was dissolved in toluene, the toluene solution was washed with water and dried over sodium sulphate and the solvent was distilled off. After recrystallisation of the residue from ligroin (boiling point 110°–140°), 1,3,5-tris-[2-(1,2,2,6,6-pentamethylpiperidin-4-yl-oxycarbonyl)-ethyl]-isocyanuric acid of melting point 177°–178° C. was obtained.

The following compounds are obtained analogously to Example 1a:

(1b) 1,3,5-tris-[2-(2,2,6,6-tetramethyl-piperidin-4-yl-oxycarbonyl)-ethyl]-isocyanuric acid, m.p. 153°–155° C.;

(1c) 1,3,5-tris-[2-(1-benzyl-2,2,6,6-tetramethyl-piperidin-4-yl-oxycarbonyl)-ethyl]-isocyanuric acid, m.p. 199°–200° C.;

(1d) 1,3,5-tris-[2-(1-allyl-2,2,6,6-tetramethyl-piperidin-4-yl-oxycarbonyl)-ethyl]-isocyanuric acid, m.p. 169°–171° C.;

(1e) 1,3,5-tris-[2-(2,2,6,6-tetramethyl-piperidino-ethoxycarbonyl)-ethyl]-isocyanuric acid, resin, analysis:
calculated: C 63.8%, H 9.28%, N 9.92%.
found: C 64.1%, H 9.0%, N 9.9%;

(1f) 1,3,5-tris-[2-(1-n-butyl-2,2,6,6-tetramethyl-piperidin-4-yl-oxycarbonyl)-ethyl]-isocyanuric acid, m.p. 152°–153° C.;

(1g) 1,3,5-tris-[2-(1-n-octyl-2,2,6,6-tetramethyl-piperidin-4-yl-oxycarbonyl)-ethyl]-isocyanuric acid, m.p. 113°–114° C.

EXAMPLE 2

1,3,5-Tris-(2-ethoxycarbonyl-ethyl)-isocyanuric acid, used as the starting material in Example 1, was prepared as follows:

10 ml of a 40% strength solution of benzyl-trimethylammonium hydroxide in methanol (Triton B) and 2.4 g of hydroquinone were added to a suspension of 77.4 g (0.6 mol) of anhydrous cyanuric acid in 500 ml of N,N-dimethylformamide. 240 g of ethyl acrylate were then added dropwise at room temperature in the course of 30 minutes, whilst stirring, and subsequently the reaction mixture was stirred for a further 7 hours at 110° (bath temperature), the cyanuric acid being completely dissolved as the reaction progressed.

For working up, most of the solvent was distilled off under a waterpump vacuum in a rotary evaporator, the residue was dissolved in diethyl ether and the solution was washed repeatedly with water. The combined ether phases were repeatedly washed with water and saturated sodium chloride solution, the ether solution was dried over sodium sulphate and the solvent was distilled off. The compound which solidifies as crystals was recrystallised from isopropanol, 1,3,5-tris(2-ethoxy-carbonyl-ethyl)-isocyanuric acid of melting point 53°–54° C. being obtained.

EXAMPLE 3a 0.85 g of tetrabutyl ortho-titanate (monomer) was added, whilst stirring, to a solution, which had been heated to 120°–125° C., of 19.35 g of 1,3,5-tris-(carbethoxy-methylene)isocyanuric acid*) and 25.4 g of 4-hydroxy-1,2,2,6,6-pentamethyl-piperidine in 130 ml of anhydrous xylene. Subsequently, whilst simultaneously passing a slow stream of nitrogen through, the reaction mixture was heated up to 136° C. in the course of 2.5 hours, during which the liberated ethanol and also xylene distilled off slowly through the descending condenser. The internal temperature of the flask was then raised to 145°–148° C. and the xylene was almost completely distilled off. For working up, the reaction mixture was dissolved in diethyl ether/dichloromethane (3:1), the solution was filtered through a layer of Hyflo, the filtrate was washed repeatedly with water and saturated sodium chloride solution and dried over sodium sulphate and the solvent was distilled off in vacuo. The crude compound which had solidified to a solid which, however, was not crystalline, was further purified by chromatography over aluminium oxide (activity II) (eluant: diethyl ether with 1.5% of methanol), pure 1,3,5-tris-[1,2.2.6.6-pentamethyl-piperidin-4-yl-oxycarbonylmethyl]-isocyanuric acid, which was then recrystallised from n-hexane, being obtained. Melting point 115°–116° C.

(*) 1,3,5-Tris-(carbethoxymethylene)-isocyanuric acid (melting point 72°–73° C., from ethanol) used as the starting material was prepared from the anhydrous trisodium salt of cyanuric acid and 3 equivalents of ethyl bromoacetate in N,N-dimethylformamide.

In an analogous manner are obtained:

(3b) 1,3,5-tris-[2.2.6.6-tetramethyl-piperidin-4-yl-oxycarbonylmethyl]-isocyanuric acid, m.p. 89°–90° C.; and (3c) 1,3,5-tris-[1-benzyl-2,2,6,6-tetramethyl-piperidin-4-yl-oxycarbonylmethyl]-isocyanuric acid, m.p. 187°–188° C.

EXAMPLE 4

0.06 mol of a freshly prepared NaOEt solution (1.4 g of Na in 50 ml of EtOH) was added dropwise in the course of 30 minutes to 34 g (0.06 mol) of bis-(3,5-di-tert.butyl-4-hydroxybenzyl)-isocyanuric acid suspended in 200 ml of ethanol.

After stirring at room temperature for one hour, 10 g (0.06 mol) of ethyl bromoacetate are added dropwise and the mixture is stirred at room temperature for 15 hours in order to keep it subsequently at reflux temperature for 6 hours. The ethanolic solution is then poured onto ice/water and the ethoxycarbonylmethyl-bis-(3,5-di-tert.butyl-4-hydroxybenzyl)-isocyanuric acid which precipitates is recrystallised from MeOH/H$_2$O. The product melts at 100° C.

EXAMPLE 4b 11.1 g (0.017 mol) of ethoxycarbonylmethyl-bis-(3,5-di-tert.butyl-4-hydroxybenzyl)-isocyanurate and 2.3 g (0.017 mol) of 4-hydroxy-1,2,2,6,6-pentamethylpiperidine are initially introduced and brought to an internal temperature of 125° C. 0.1 g of lithium amide is added and elimination of ethanol starts spontaneously. The internal temperature is raised to 140° C. and, after allowing the reaction to proceed for 2 hours at the above temperature, a vacuum (60 mm Hg) is applied for ½ hour at an internal temperature of 150° C. After cooling, the residue is taken up in toluene, the solution is neutralised with glacial acetic acid and the organic phase is extracted with water and dried over sodium sulphate. In this way, 1-[(1,2,2,6,6-pentamethylpiperidin-4-yl-oxycarbonyl)-methyl]-3,5-bis-(3,5-di-tert.butyl-4-hydroxybenzyl)-isocyanuric acid is obtained as an amorphous residue.
Analysis:
calculated: C 65.56, H 8.82, N 7.21,
found: C 69.6, H 8.7, N 6.7.

EXAMPLE 4c

Using 3,5-di-tert.butyl-4-hydroxybenzyl-isocyanuric acid and ethyl bromoacetate as the starting materials, 1-3-bis-[(1,2,2,6,6-pentamethyl-piperidin-4-yl-oxycarbonyl)-methyl]-5-[3,5-di-tert.butyl-4-hydroxybenzyl]-isocyanuric acid is obtained, as an amorphous powder, under analogous conditions.

EXAMPLE 5

38.1 g of 4-(chloroacetylamino)-1,2,2,6,6-pentamethylpiperidine (m.p. 117°–118° C.; produced from 4-amino-1,2,2,6,6-pentamethyl-piperidine, chloroacetyl chloride and triethylamine) were added portionwise at 80° C., with vigorous stirring, to a suspension of 9.8 g of anhydrous trisodium isocyanurate in 90 ml of dimethylformamide, and the mixture was heated for 60 hours at 100°–105° C. For working up, the reaction mixture was cooled to room temperature and filtered; the suction-filter residue was subsequently washed with dichloromethane, and the filtrate was freed in vacuo from the solvents. The residue was suspended in 400 ml of water, and repeatedly extracted with dichloromethane. The combined dichloromethane phases were washed with water and dried over sodium sulphate, and the solvent was distilled off. The compound obtained in crystalline form was recrystallised in acetonitrile/methyl ethyl ketone (1:1) to yield pure 1,3,5-tris-[1,2,2,6,6-pentamethyl-piperidine-4-aminocarbonylmethyl]-isocyanuric acid, m.p. 200°–202° C.

Analysis:
calculated: C 61.6%, H 9.15%, N 16.59%,
found: C 61.3%, H 9.2%, N 16.4%.

EXAMPLE 6

12 g of 1,3,5-tris-[2-(2,2,6,6-tetramethyl-piperidin-4-yl-oxycarbonyl)-ethyl]-isocyanuric acid (m.p. 153°–155° C.) were suspended in 120 ml of acetic anhydride, and the suspension was heated at 95° C. for 26 hours. The acetic anhydride was then distilled off as completely as possible, in a water-jet vacuum, from the clear solution formed; the residue was dissolved in 200 ml of diethyl ether/methylene chloride (9:1), the solution was washed twice with water, three times with saturated sodium hydrogen carbonate solution, and finally again twice with water. The organic phase was dried over sodium sulphate, the solvent was distilled off in vacuo, and the residue was recrystallised from diethyl ether/acetonitrile (98:2) to obtain pure 1,3,5-tris-[2-(1-acetyl-2,2,6,6-tetramethyl-piperidin-4-yl-oxycarbonyl)-ethyl]-isocyanuric acid, m.p. 126.5°–128° C.

1,3,5-Tris-[2-(1-acetyl-2,2,6,6-tetramethyl-piperidin-4-yl-oxycarbonyl)-ethyl]-isocyanuric acid can also be produced analogously to Example 1 by transesterification of 1,3,5-tris(2-ethoxycarbonyl-ethyl)-isocyanuric acid with 3 equivalents of 1-acetyl-2,2,6,6-tetramethyl-4-hydroxy-piperidine (m.p. 102°–104° C.).

EXAMPLE 7

0.8 g of tetrabutyl-ortho-titanate (monomer) was added, with stirring, to a solution heated to 130° of 23.6 g of 1,3,5-tris(3-ethoxycarbonyl-propyl)-isocyanuric acid (0.05 mol) and 25.7 g (0.15 mol) of 4-hydroxy-1,2,2,6,6-pentamethyl-piperidine in 200 ml of anhydrous xylene [the 1,3,5-tris-(3-ethoxycarbonylpropyl)-isocyanuric acid serving as starting material was produced from the anhydrous trisodium salt of cyanuric acid and 3 equivalents of ethyl 4-bromobutyrate in dimethylformamide at 130° C.]. The reaction mixture was thereupon heated, as a gentle stream of nitrogen was simultaneously being passed through, in the course of 5 hours to 135° C., with the liberated ethanol and also xylene being distilled off through the attached descending condenser. The internal temperature was subsequently raised to 145°–150° C.; it was maintained there for a further 4 hours and the xylene was distilled off as completely as possible. The residue after cooling was dissolved in methylene chloride, washed three times with 0.1 N acetic acid and twice with water, and filtered clear through a layer of Hyflo. The filtrate was dried over sodium sulphate, and the solvent was distilled off in vacuo. The residue was further purified chromatographically on silica gel (eluant: diethyl ether/triethylamine 96:4) to yield, after the complete removal of the solvent under high vacuum, pure 1,3,5-tris-[3-(1,2,2,6,6-pentamethyl-piperidin-4-yl-oxycarbonyl)-propyl]-isocyanuric acid in the form of highly viscous colourless oil.

Analysis: $C_{45}H_{78}N_6O_9$
calculated: C 63.8%, H 9.28%, N 9.92%,
found: C 63.9%, H 9.2%, N 9.9%.

EXAMPLE 8a 100 parts of polypropylene powder (Moplen, fibre grade, from Messrs. Montedison) are homogenised for 10 minutes at 200° C., in a Brabender plastograph, with 0.2 part of octadeyl $\beta$-(3,5-di-tert.-butyl-4-hydroxyphenyl)-propionate and 0.25 part of one of a stabiliser in the following Table 1. The composition thus obtained is removed from the kneader as rapidly as possible and pressed in a toggle press to give a 2–3 mm thick sheet. Part of the resulting pressed blank is cut out and pressed between two high-gloss hard aluminum foils, using a manual hydraulic laboratory press, for 6 minutes at 260° C. and under a pressure of 12 tonnes to give a 0.5 mm thick sheet, which is immediately chilled in cold water. The 0.1 mm thick test sheet is produced from this 0.5 mm sheet under precisely the same conditions. 60×44 mm portions are now punched from this test sheet and exposed in the Xenotest 150. These test pieces are taken from the exposure apparatus at regular intervals and their carbonyl content is tested in an IR spectrophotometer. The increase in the carbonyl extinction at 5.85μ on exposure is a measure of the photooxidative degradation of the polymer (see L. Balaban et al., J. Polymer Sci., Part C, 22, 1059–1071 (1969); J. F. Heacock, J. Polymer Sci., Part A-1, 22, 2921–34 (1969) and D. J. Carlsson and D. M. Wiles, Macromolecules 2, 587–606 (1969)) and, according to experience, is associated with a deterioration in the mechanical properties of the polymer. Thus, for example, the sheet is completely brittle on attainment of a carbonyl extinction of about 0.300.

The protective action of the stabilisers according to the invention can be seen from the following Table 1

TABLE 1

| Stabiliser Example No. | Exposure time in hours until the carbonyl extinction is 0.300 |
| --- | --- |
| comparison | 1180 |
| 4b | 3000 |
| 4c | 5870 |
| 1b | 6700 |
| 1a | 6110 |
| 3b | 4300 |
| 3a | 5000 |

EXAMPLE 8b

Analogous to Example 8a except that a Xenotest 1200 was used instead of a Xenotest 150.

TABLE 2

| Stabilizer Example No. | Exposure time in hours until extinction is 0.300 |
|---|---|
| comparison | 470 |
| 1c | 1900 |
| 1d | 1900 |
| 6 | 1900 |

EXAMPLE 9

100 parts of polypropylene (melt index 3.2 g/10 min., 230°/2160 g) are thoroughly mixed for 10 minutes, in a shaking apparatus, with 0.2 part of one of the stabilisers given in the following Table 3. The mixture obtained is kneaded in a Brabender plastograph at 200° C. for 10 minutes; the material obtained in this manner is then pressed out in a platen press at 260° C. platen temperature to form 1 mm thick sheets, from which are stamped strips 1 cm wide and 17 cm long.

The test for effectiveness of the additives contained in the test strips is carried out by heat ageing in an air-circulation furnace at 135° C. and 149° C., with an additive-free test strip serving as a comparison. Three test strips are used for each formulation. The end point of the test is defined as the point at which an easily visible crumbling of the test strip commences.

TABLE 3

| Stabiliser Example No. | Days until decomposition commences | |
|---|---|---|
|  | 145° C. | 135° C. |
| 4b | 27 | 67 |
| 4c | 27 | 68 |

EXAMPLE 10

Some of the test specimens described in Example 9 are tested in addition for colour stability as follows:

(a) after incorporation (Table IV, column 2), (b) after 500 hours of exposure to light in a Xenotest apparatus of the firm Hanau (Table IV, column 3), (c) after treatment for 1 week with boiling water (Table IV, column 4).

For the evaluation, an empirical colour scale is used in which 5 signifies colourness, 4 a slight discolouration just perceptible, and 3, 2 and 1 signify a successively more intense discolouration.

TABLE IV

| Stabiliser Example No. | Colour evaluation according to scale 1-5 | | |
|---|---|---|---|
|  | after incorporation | after exposure to light | boiling water 1 week |
| 4b | 4-5 | 5 | 4 |
| 4c | 4-5 | 5 | 4-5 |

What is claimed is:

1. A compound of the formula I

or an addition salt thereof,
in which $R_1$ is

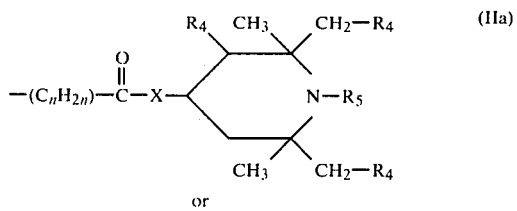

or

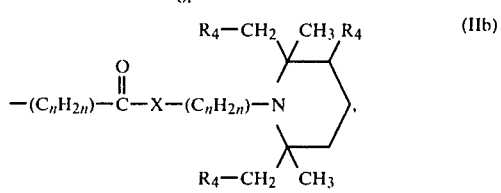

and $R_2$ and $R_3$ independently of one another are hydrogen, a group of the formula IIa or IIb or addition salts thereof, or —$CH_2R_{11}$, wherein n is 1, 2, 3, 4 or 5, $R_4$ is hydrogen or $C_1$-$C_8$ alkyl and $R_5$ is hydrogen, oxyl, $C_1$-$C_{12}$ alkyl, $C_3$-$C_6$ alkenyl, $C_3$-$C_4$ alkinyl, $C_2$-$C_{21}$ alkoxyalkyl, $C_7$-$C_9$ aralkyl, 2,3-epoxypropyl, an aliphatic acyl group with 1–4 C atoms or one of the groups —$CH_2COOR_6$, —$CH_2$—$CH(R_7)$—$OR_8$, —$COOR_9$ or —$CONHR_9$, wherein $R_6$ is $C_1$-$C_{12}$ alkyl, $C_3$-$C_6$ alkenyl, phenyl, $C_7$-$C_8$ aralkyl or cyclohexyl, $R_7$ is hydrogen, methyl or phenyl, $R_8$ is hydrogen, an aliphatic, aromatic, araliphatic or alicyclic acyl group with 1–18 C atoms, wherein the aromatic part is unsubstituted or is substituted by at least one member of the group chlorine, $C_1$-$C_4$ alkyl, $C_1$-$C_8$ alkoxy and hydroxyl, and $R_9$ is $C_1$-$C_{12}$ alkyl, cyclohexyl, phenyl or benzyl and X is —O— or —$NR_{10}$— wherein $R_{10}$ is hydrogen or $C_1$-$C_{12}$ alkyl, and $R_{11}$ is one of the groups

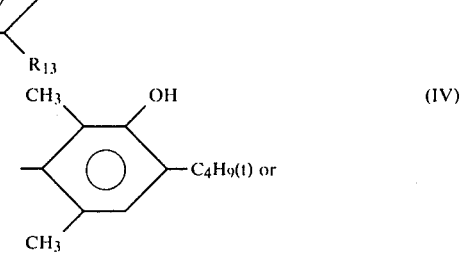

-continued

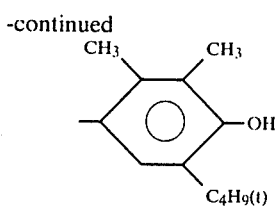

wherein R$_{12}$ and R$_{13}$ independently of one another are C$_1$-C$_{12}$ alkyl, C$_5$-C$_{12}$ cycloalkyl, C$_7$-C$_9$ aralkyl or C$_7$-C$_{12}$ alkaryl.

2. A compound according to claim 1 of the formula I, in which R$_1$ is a group of the formula IIa, R$_2$ and R$_3$ independently of one another are a group of the formula IIa or —CH$_2$—R$_{11}$, n is 1, 2, 3, 4 or 5, R$_4$ is hydrogen or C$_1$-C$_4$ alkyl and R$_5$ is hydrogen, oxygen, C$_1$-C$_8$ alkyl, C$_3$-C$_4$ alkenyl, C$_3$-C$_4$ alkinyl, C$_2$-C$_6$ alkoxyalkyl, C$_7$-C$_9$ aralkyl, acetyl, acryloyl or crotonoyl or one of the groups —CH$_2$—COOR$_6$, —CH$_2$—CH(R$_7$)—OR$_8$, —COOR$_9$ or —CONHR$_9$, wherein R$_6$ is C$_1$-C$_4$ alkyl, C$_3$-C$_4$ alkenyl, phenyl, C$_7$-C$_8$ aralkyl or cyclohexyl, R$_7$ is hydrogen, methyl or phenyl, R$_8$ is hydrogen or an aliphatic, aromatic, alicyclic or araliphatic acyl group with 1-18 C atoms, wherein the aromatic part is unsubstituted or is substituted by at least one member of the group of chlorine, C$_1$-C$_4$ alkyl, C$_1$-C$_8$ alkoxy and hydroxyl, R$_9$ is C$_1$-C$_{12}$ alkyl, X is —O— or —NR$_{10}$— wherein R$_{10}$ is hydrogen or C$_1$-C$_{12}$ alkyl, and R$_{11}$ is one of the groups of the formula III, IV or V, wherein R$_{12}$ and R$_{13}$ independently of one another are C$_1$-C$_8$ alkyl, C$_5$-C$_6$ cycloalkyl or C$_7$-C$_9$ aralkyl.

3. A compound according to claim 1, of the formula I, in which R$_1$ is a group of the formula IIa, R$_2$ and R$_3$ independently of one another are a group of the formula II or —CH$_2$—R$_{11}$, n is 1, 2 or 3, R$_4$ is hydrogen or methyl, R$_5$ is hydrogen, C$_1$-C$_4$ alkyl, allyl, propargyl, C$_2$-C$_6$ alkoxyalkyl, acetyl, acryloyl or crotonoyl or one of the groups —CH$_2$—COOR$_6$, —CH$_2$—CH(R$_7$)—OR$_8$, —COOR$_9$ or —CONHR$_9$ wherein R$_6$ is C$_1$-C$_4$ alkyl, R$_7$ is hydrogen or methyl, R$_8$ is hydrogen and R$_9$ is C$_1$-C$_4$ alkyl, X is —O— or —NR$_{10}$— wherein R$_{10}$ is hydrogen or methyl, and R$_{11}$ is a group of the formula III, IV or V wherein R$_{12}$ and R$_{13}$ independently of one another are C$_1$-C$_4$ alkyl.

4. A compound according to claim 1 of the formula I, in which R$_1$, R$_2$ and R$_3$ each are a radical of the formula IIa, n is 1, 2 or 3, R$_4$ is hydrogen, R$_5$ is hydrogen, methyl or an aliphatic acyl group of 1-4 C atoms and X is —O— or —NH—.

5. A compound according to claim 1 of the formula I wherein n is 1 and at least one of R$_1$ and R$_3$ represents the formula IIa.

6. A compound according to claim 1 wherein at least one of R$_1$, R$_2$ and R$_3$ represents the formula IIb.

7. A compound according to claim 1 said compound being 1,3,5-tris-[2-(1,2,2,6,6-pentamethyl-piperidin-4-yl-oxycarbonyl)-ethyl]-isocyanuric acid.

8. A compound according to claim 1 said compound being 1,3,5-tris-[2-(2,2,6,6-tetramethyl-piperidin-4-yl-oxycarbonyl)-ethyl]-isocyanuric acid.

9. A 2,2,6,6-tetrasubstituted-4-piperidyl carboxy heterocyclic compound having the general formula:

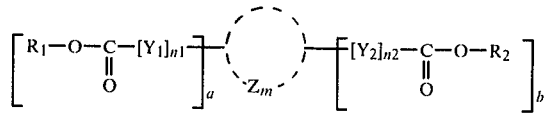

wherein:

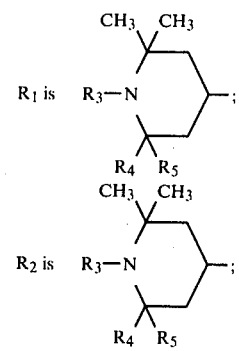

R$_3$ is selected from the group consisting of hydrogen; oxyl; alkyl; alkenyl; alkynyl; and aralkyl;
R$_4$ is C$_1$-C$_9$ alkyl and R$_5$ is methyl;
a is selected from the group consisting of 1,2 and 3;
b is selected from the group consisting of 0, 1 and 2;
Z represents

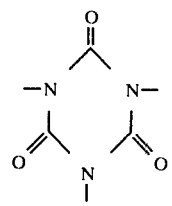

;
m is 1;
Y$_1$ and Y$_2$ are alkylene, the alkylene having from one to four carbon atoms; and
n$_1$ and n$_2$ are 1.

10. A compound according to claim 9 in which a is 1 and b is zero.

11. A compound according to claim 9 in which a is 1 and b is 1.

12. A compound according to claim 9 in which n$_1$ and n$_2$ are each 1 and Y$_1$ and Y$_2$ are each alkylene.

13. A compound according to claim 12 in which Y$_1$ and Y$_2$ are each CH$_2$.

14. A compound according to claim 13 in which Y$_1$ and Y$_2$ are each C$_2$H$_4$.

* * * * *